United States Patent [19]

Atlee, III et al.

[11] 4,387,723
[45] Jun. 14, 1983

[54] METHOD AND APPARATUS FOR DETERMINING THE LEVEL OF NEUROMUSCULAR BLOCK IN A PATIENT

[75] Inventors: John L. Atlee, III, Deforest, Wis.; Maximillian D. Fiore, Livermore, Calif.

[73] Assignee: Wisconsin Alumni Research Foundation, Madison, Wis.

[21] Appl. No.: 214,783

[22] Filed: Dec. 9, 1980

[51] Int. Cl.$^3$ ............................................. A61B 5/05
[52] U.S. Cl. .................................. 128/734; 128/741; 128/782
[58] Field of Search .............................. 128/733–734, 128/741, 744, 774, 782, 639–640, 796, 420 A, 420 R, 421, 422, 423 R, 423 W; 33/DIG. 13

[56] References Cited

U.S. PATENT DOCUMENTS

| 3,364,929 | 1/1968 | Ide et al. ............................. 128/741 |
| 3,565,080 | 7/1967 | Ide et al. |
| 3,810,457 | 10/1972 | Bottcher et al. |
| 3,898,983 | 10/1973 | Elam |
| 3,898,983 | 8/1975 | Elam ................................... 128/741 |
| 4,236,528 | 12/1980 | Stanec et al. ....................... 128/782 X |
| 4,291,705 | 9/1981 | Severinghaus et al. ............ 128/733 |

OTHER PUBLICATIONS

Miller, Ronald D., Antagonism of Neuromuscular Blockade. Anesthesiology, vol. 44, No. 4, pp. 318–329, Apr. 1976.
Specification of Grass Force-Displacement Transducers, Models FT .03 and FT 10, May, 1977.
Product description sheet for Model NS-2 Peripheral Nerve Stimulator, Professional Instruments Co., Houston, Texas.
Product description sheet Emerson Relaxaid, J. H. Emerson Company, Cambridge, Massachusetts.
Medical Instrumentation, vol. 12, No. 2, Mar.–Apr. 1978, pp. 92–93.
Troke; "The Direct Reading D.C. Strain-Gage Bridge; *Instruments,* vol. 24; Apr. 1951; pp. 400–401, 450–452, 454, 456 and 458.
Pavlov et al.; "Neuromuscular Block Indicator"; *Biomed. Eng.,* vol. 13, No. 4; Jul.–Aug. 1979; Publ. Mar. 1980, pp. 205–207.

*Primary Examiner*—Lee S. Cohen
*Assistant Examiner*—Angela D. Sykes
*Attorney, Agent, or Firm*—Isaksen, Lathrop, Esch, Hart & Clark

[57] ABSTRACT

Electrical stimulus pulses are provided to the ulnar nerve of a patient and the adduction of the patient's thumb in response to the pulses is measured by a strain gage force transducer attached to the thumb and wrist of the patient. The force transducer provides an electrical output signal proportional to the magnitude of the thumb response, and this signal is subsequently amplified, filtered, digitized and then provided to a controller which includes a microprocesser. In a preferred procedure for determining the level of neuromuscular block in a patient by estimating twitch height depression without using control responses, a train of four pulses is applied to the patient over a two second interval, and a magnitude of the response as measured by the transducer is received and stored by the microprocesser. The four response magnitude peaks are then individually compared to preselected threshold values, and the degree twitch height depression estimated based on whether or not the response peaks are above or below the threshold levels, and indicia showing the degree of estimated twitch height depression is displayed to the operator.

14 Claims, 6 Drawing Figures

METHOD AND APPARATUS FOR DETERMINING THE LEVEL OF NEUROMUSCULAR BLOCK IN A PATIENT

TECHNICAL FIELD

This invention pertains generally to the field of instrumentation for determining the degree of neuromuscular block existing in an anesthesized patient.

BACKGROUND ART

Neuromuscular blocking drugs, or muscle relaxants, are widely used by anesthetists for producing muscle relaxation during anesthesia and surgery. Controlled muscle paralysis in the patient is commonly used for tracheal intubation, surgical relaxation and to permit controlled breathing in thoracic surgical procedures.

Muscle relaxants may be classified as either competitive non-depolarizing) or non-competitive (depolarizing) agents. Non-depolarizing relaxants compete with acetylcholine for receptor sites located at the myoneural junction, and block muscle contraction in response to acetylcholine released following nerve stimulation. Depolarizing relaxants, conversely, have an action similar to that of acetylcholine, and block by persistent depolarization of muscle tissue. With both type of relaxants, neuromuscular block persists as long as the quantity of relaxant introduced into the patient has not been completely bound or metabolized.

The type (depolarizing or non-depolarizing) and the magnitude of neuromuscular block can be assessed by stimulating a peripheral motor nerve and observing or measuring the force of contraction of the muscle supplied by that nerve. This is usually done in a clinical setting by stimulating the ulnar nerve at the wrist or elbow and monitoring the force of contraction (adduction) of the thumb as the *adductor pollicis* muscle contracts. The force of contraction is measured using a force-displacement transducer which provides an electrical output signal proportional to the force supplied by the thumb during contraction.

The pattern of evoked muscle response to changes in the frequency of the electrical stimulation allows the type and quantitative level of neuromuscular block to be determined. Stimuli commonly used include (1) short durartion, single pulses, which yield a twitch response, (2) a train of four pulses at short intervals which produce a train of four responses, and (3) a five second period of application of a rapid succession of pulses (e.g., at pulse frequencies 30, 50, 100 or 200 Hz) which produces a tetanic response.

When single twitch responses are to be observed in a clinical setting, a control response is obtained by applying a supramaximal, square-wave stimulus (preferably no longer than 200 microseconds in duration) prior to the administration of the muscle relaxant and measuring the magnitude of the resulting response. The responses that are obtained to the pulse stimuli following the administration of relaxants are compared to the control response, and the degree of depression of muscle response is estimated or quantitated by comparing the magnitude of the responses obtained to the magnitude of the control response. A major disadvantage of using a single twitch response to estimate the level of neuromuscular block is that a control response must be obtained before a muscle-relaxant, or any other anesthetic drug, is administered.

The need for first obtaining a control response may be eliminated if a train-of-four stimulation procedure is used. Four pulses are applied in succession at 2 Hz, and the amplitude of the fourth twitch response during supramaximal stimulation is compared to the amplitude of the first twitch response; the ratio between the two ($T_4$ ratio) is then calculated to provide an estimate of the level of twitch height depression. The estimate of the level of single twitch height depression can then be correllated with clinical neuromuscular functions such as adequacy of respiration, cough response, and surgical relaxation. A $T_4$ ratio greater than 75% indicates normal neuromuscular function, while a ratio less than 75% indicates the presence of impaired function. The estimate of twitch height depression when the $T_4$ ratio is less than 75% may be further quantitated by noting the presence or absence of twitch responses following the first, second, and third pulse stimuli in a train-of-four pulses.

Tetanic stimulation is the most sensitive clinically employed test of neuromuscular function. The tetanic response may be obtained by applying 5 seconds of supermaximal pulse stimulation at frequencies of 30, 50, 100, or 200 Hz. The ability of the muscle to sustain contraction during tetanic stimulation varies with the level of neuromuscular block. In addition to the need for an awake control response, major disadvantages of tetanic stimulation are that it alters neuromuscular function and is painful to patients who are awake. These disadvantages make it difficult to quantitate the degree of neuromuscular block with tetanic stimulation and tetanic stimulation is presently used mainly for clinical research.

In current clinical practice, the degree of neuromuscular block is most commonly estimated by observing and qualitatively assessing the muscle response following single twitch or train-of-four stimulation. While this method is imprecise and not totally satisfactory, currently available apparatus for quantitatively assessing neuromuscular function are relatively costly and difficult for the clinician to use.

DISCLOSURE OF THE INVENTION

In accordance with the invention, a preferred stimuli consisting of a train-of-four pulses is applied to the skin of a patient over the ulnar nerve at a location (elbow or forearm) which will permit supramaximal stimulation of the thumb adductor (*adductor pollicis*) muscle. By employing a train-of-four stimulation pulse, it is not necessary to obtain control measurements before administration of muscle relaxants in order to determine the degree of neuromuscular block. The train-of-four response is used to estimate the level of twitch response depression that would have been observed if a suitable twitch control could have been obtained. Such an estimate is useful where a twitch control response cannot be obtained because the patient is already asleep or other drugs affecting neuromuscular function are present. The estimate of twitch depression can be used to estimate the level of neuromuscular block and, in turn, the adequacy of neuromuscular function. For example, if a patient has 5% or less twitch depression, neuromuscular function is adequate for normal breathing and coughing. If the twitch response is more than 75% depressed, surgical relaxation is present and neuromuscular function will not be adequate to permit normal breathing and coughing.

The adduction of the thumb of a patient in response to each of the four electrical stimuli is measured to determine the magnitude of the force response; this information may then be utilized to estimate the level of twitch depression. For example, the response to the first stimulus pulse may be below a threshold magnitude previously determined to indicate nearly complete (95%) twitch height depression. The threshold level can be selected, for example, to be just above the expected maxima of system noise and normal, unstimulated thumb movements. If the first peak is above the threshold magnitude, and within a time range after stimulation in which valid response peaks are expected to be found it is then determined if a second peak is present, i.e., above a threshold magnitude. If the second peak is below such a threshold, it is expected that the patient has experienced approximately 90% twitch depression. However, if the second peak is above the threshold, it is then determined if a third peak is above a threshold magnitude. If no third peak is found greater than the threshold, it can be predicted that the patient has experienced 75% twitch height depression. If the third peak is present (above the threshold), it is then determined if a fourth response peak exists and is above a threshold. If not, 70% twitch height depression can be predicted. If a fourth peak is found above the threshold level, the magnitudes of the fourth peak and the first peak are compared and the ratio of the two calculated. If the ratio of the fourth response peak to the first peak exceeds 75%, then the level of twitch depression is expected to be 5% or less, whereas if the ratio is less than 75%, the level of twitch depression may be expected to be 50% or more. The calculation of the ratio of the fourth to first response peaks provides a convenient and quantitative means for the anesthetist to estimate the degree of twitch depression, which, in turn, can be used to predict the adequacy of neuromuscular function (during recovery) or the level of block in unconcious patients.

The apparatus for carrying out the steps of the invention utilizes a stimulator to apply an electrical stimulus to the patient's ulnar nerve, a force/displacement transducer attachable to the hand and thumb of a patient to measure the adduction response of the thumb and produce an electrical signal proportional to the response, a signal amplifier and filter receiving the electrical signal from the transducer, and an analog-to-digital converter which converts the signal from the amplifier to digital form and delivers it to a controller which preferably includes a microcomputer. The controller quantitates and compares the various peaks in the response, in the manner described above, and delivers a signal to a display panel which indicates to the operator the estimated level of twitch depression. The controller delivers control signals to the nerve stimulator to activate it at predetermined times.

The transducer which monitors the thumb adduction response of the patient includes a resiliently bendable beam extending from the wrist to the end of the thumb, a wrist collar mounted on one end of the bendable beam and releasably secured to the wrist, a thumb collar mounted to the other end of the beam and releasably secured to the patient's thumb, and four electrical resistance strain gages mounted in pairs on each side of the beam intermediate its ends and adapted to measure the tension and compression, respectively, in the beam as the thumb adducts in response to the electrical stimuli. The four strain gages are connected in a bridge circuit with the members of each pair of strain gages connected in opposite arms of the bridge so that any changes in the configuration of the beam due to changes in temperature and other conditions are balanced out. A low-voltage battery supplies bias voltage across two terminals of the bridge, and the response of the patient is measured by the change in voltage across the other terminals of the bridge as the resistances of each pair of strain gages change as the beam is bent. The strain gages are preferably biased by a low voltage battery, rather than line power, to completely isolate the patient from line voltages.

The peripheral nerve stimulator is also preferably supplied by a battery, and is isolated from line power so that the patient is not exposed to potential shocks. Because of their relative high power consumption, the controller, analog-to-digital converter, and display unit are supplied with line power, and thus the control signals from the controller are preferably passed through isolation devices such as opto-isolators before being transmitted to the nerve stimulator so that the potential for shocks is reduced as much as possible.

The controller, which preferably utilizes a microprocessor coupled with RAM and ROM memory units, determines, in the manner of the method outlined above, whether the patient response signals indicate neuromuscular block and, if so, the estimated level of twitch suppression. The microprocessor outputs this information to a display unit so that the anesthetist can determine the level of neuromuscular function present.

Further objects, features and advantages of the invention will be apparent from the following detailed description taken in conjunction with the accompanying drawings showing preferred embodiments of the invention.

BEST MODE FOR CARRYING OUT THE INVENTION

Figure 1:
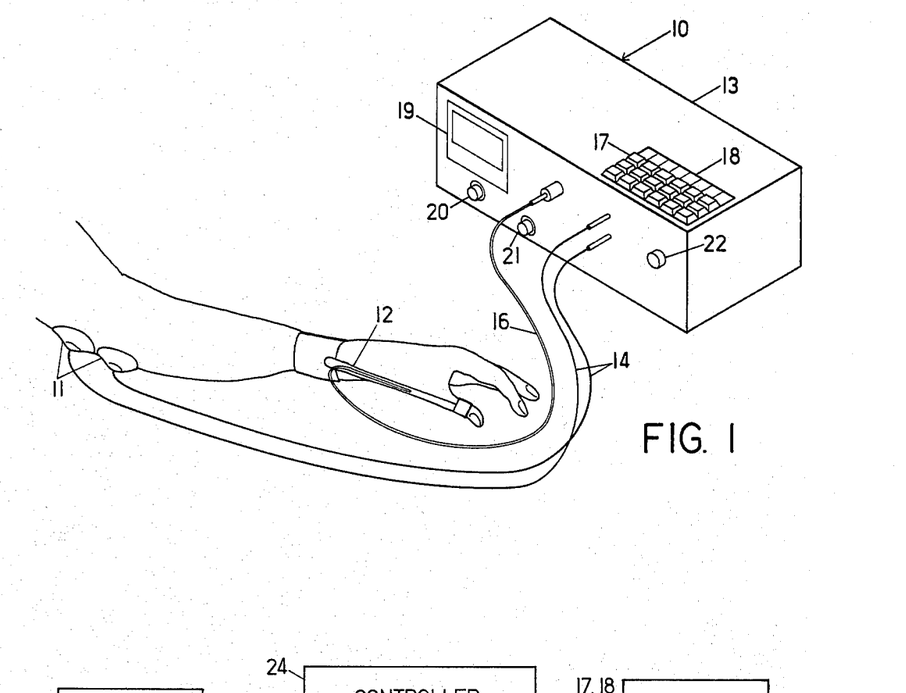
FIG. 1 is a perspective view of the apparatus of the invention attached to the forearm, wrist and thumb of a patient.

With reference to the drawings, an illustrative perspective view of the apparatus of the invention is shown generally at 10 in FIG. 1 with electrodes 11 and a force/displacement transducer 12 attached to the arm and hand respectively of a patient. The stimulation signals are transmitted from the cabinet 13 of the apparatus through wires 14 to the electrodes 11. These electrodes are preferably surface ECG monitoring electrodes which transmit the electrical stimulus signal through the skin to the ulnar nerve. Since the surface area of these electrodes is relatively large, the stimulation does not cause tissue damage; however, since there can be some current spread with such large area electrodes, the electrodes are carefully positioned over the ulnar nerve to insure that the nerve, and not muscle, is directly stimulated. Smaller pediatric ECG monitoring electrodes provide the best results, since the smaller surface area of these electrodes helps to minimize excessive current spread. The electrodes are preferably placed over the ulnar nerve at the wrist or over the ulnar groove at the elbow.

The output from the transducer 12 is passed through a coupling wire 16 back to the cabinet 13. The operator can provide instructions to the apparatus through a key pad 17, and output indicative of the predicted level of twitch height depression is communicated to the operator by an LED display 18. A meter 19 is provided with the apparatus to monitor the level of output from the transducer 12, and the biasing of the transducer can be adjusted by a control knob 20. Another knob 21 is provided to allow adjustment of the gan of the output from the transducer, and a small audio alarm device 22, such as a buzzer, is provided to alert the operator when potentially erroneous response readings are being received by the apparatus.

Figure 2:
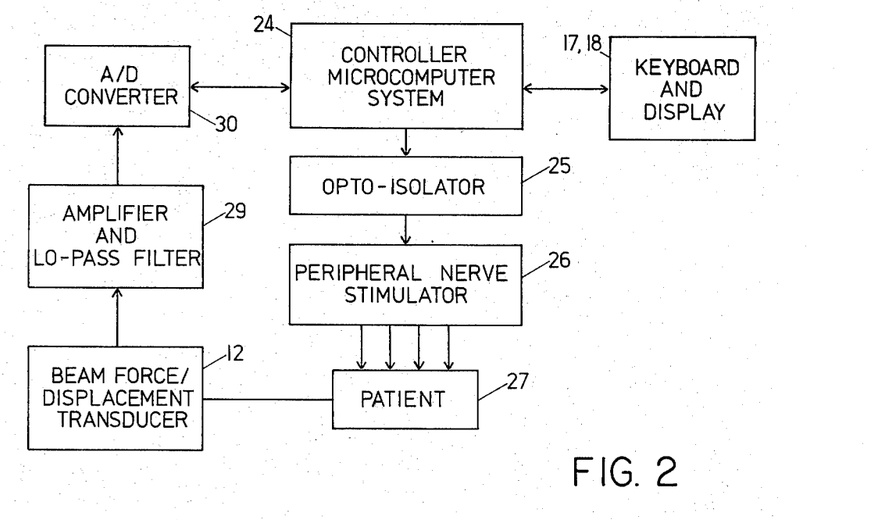
FIG. 2 is a block diagram of the major functional components of the apparatus of the invention.

The operation of the apparatus is best shown with reference to the block diagram view of FIG. 2. A controller 24 initiates the application of the stimulation pulses and records the magnitude of the response detected by the displacement transducer 12. In the preferred embodiment, the controller 24 comprises a micro-computer system which is adapted to receive the response magnitude data in digitized form, process the data, and provide output signals to the display 18. However, it is apparent to those skilled in the art that the operations on the data can as well be accomplished by ananlog or special purpose digital components, although the utilization of a programmable microprocesser is preferred because of adaptability and lower cost.

The controller 24 provides control signals at the preferred time of stimulation through an opto-isolator unit 25 and thence to the peripheral nerve stimulator unit 26. The nerve stimulator 26 is preferably powered by a low-voltage battery and the opto-isolator 25 is provided to insure complete isolation of the patient from line voltages. The series of pulses provided from the nerve stimulator 26 through the electrodes 11 to the ulnar nerve cause a response in the patient—adduction of the thumb—which is measured by the force/displacement transducer 12. This unit provides an output signal indicative of the magnitude of the thumb displacement, and this signal is passed through an amplifier and low pass filter unit 29 to an analog-to-digital converter 30 which transmits the response signals in digitized form to the controller 24. A low pass filter within the unit 29, preferably having a cut-off frequency of approximately 10 Hz., filters out extraneous signals above the frequency range of thumb response motions of interest. The response signal is also preferably amplified by the unit 29 to provide a signal of convenient magnitude to the analog-to-digital converter 30.

Figure 3:
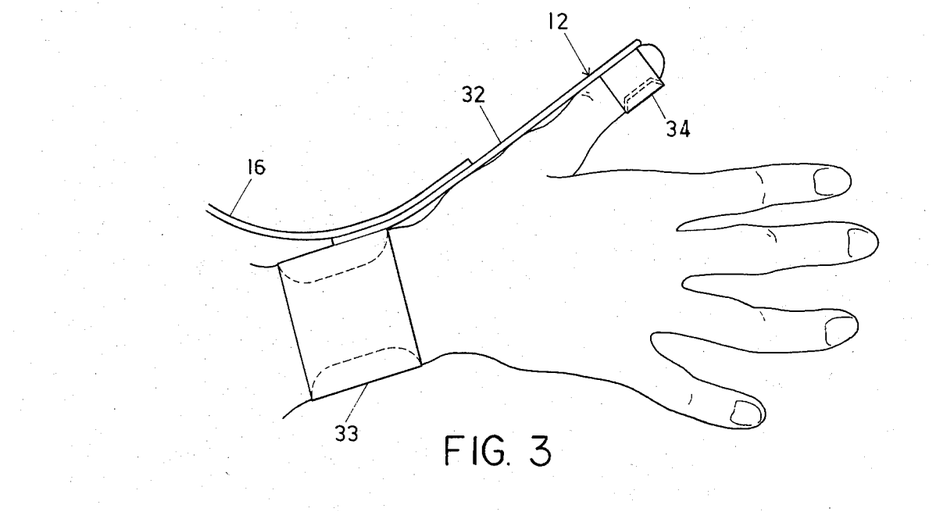
FIG. 3 is a plan view of a right hand model of a force/displacement transducer in accordance with the invention shown mounted on the right hand of a patient.
Figure 4:
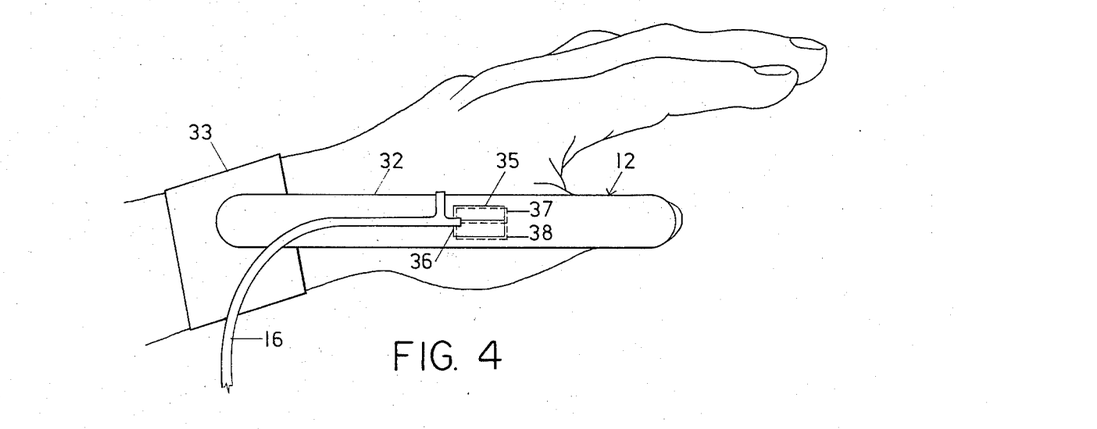
FIG. 4 is a side view of a left hand version of a force/displacement transducer in accordance with the invention shown mounted on the left hand of the patient.

The force/displacement transducer 12 is shown in a right hand version in FIG. 3 and in a left-hand version in FIG. 4. With reference to the view of FIG. 3, the transducer 12 includes a resiliently bendable beam 32 which is elongated and has substantially flat opposite sides, one side of which extends along the thumb and wrist of the patient. A wrist restraining collar 33 is rigidly mounted to one end of the beam 32 and a thumb restraining collar 34 is rigidly mounted to the other end of the beam. The collars 34 and 33 are preferably formed as shown, comprising a band of relatively easily bent metal which extends partially around the wrist or thumb, respectively, of the patient and which can be bent apart to allow insertion onto the wrist or thumb and then bent together to securely hold the wrist or thumb. The beam itself must be bendable but unyielding, so that the bending displacement of the beam is substantially proportional to the force applied by the thumb throughout the range of response produced by adduction of the thumb. A satisfactory material for the beam is a molybdenum-steel alloy, which bends readily and substantially linearly with the applied force. The transmitting wire 16 extends down to the surface of the beam 32 and is attached to the strain gages 35, 36, 37 and 38 on the beam surfaces. The patient's hand and wrist must be positioned and held on a flat surface so that the only force measured by the transducer 12 is thumb adduction.

Figure 5:
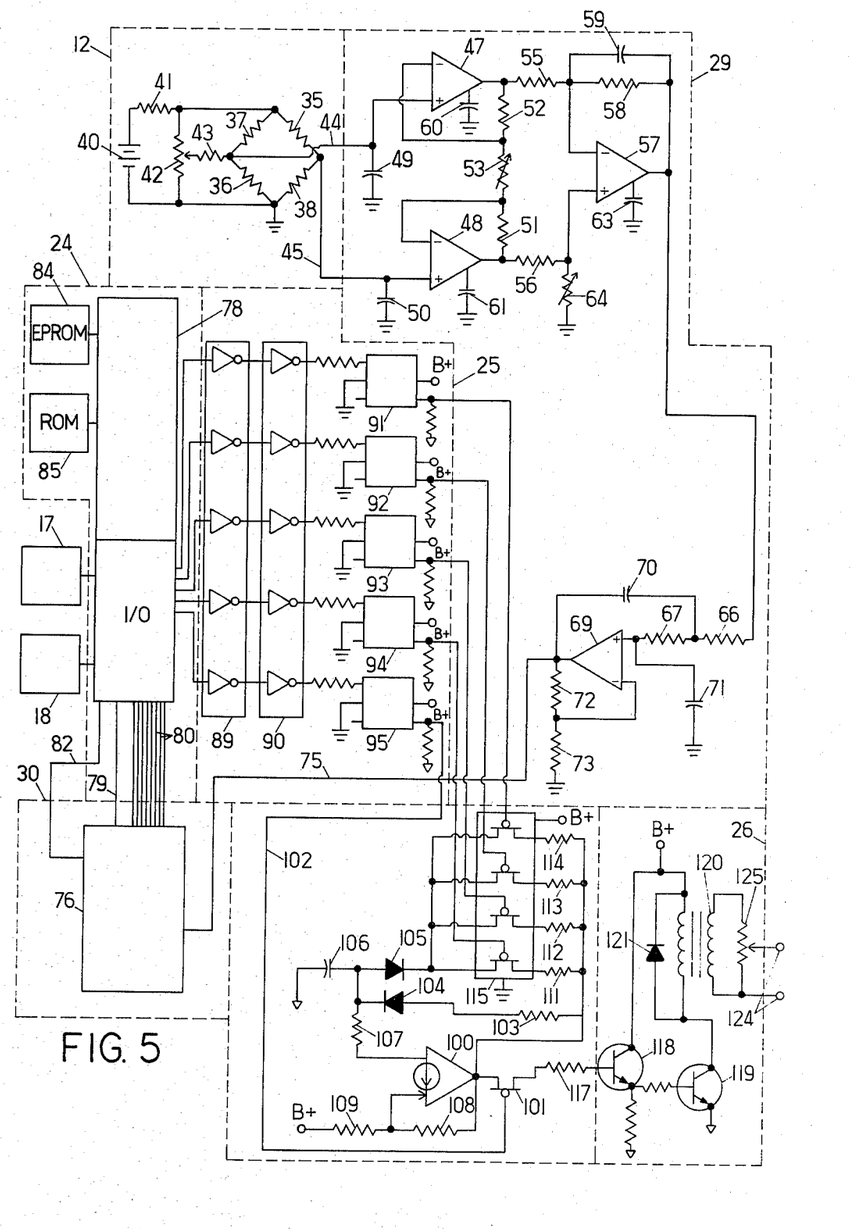
FIG. 5 is a schematic diagram of the electronic components of the apparatus.

The mounting of the strain gages is shown in the view of FIG. 4, a left-hand version of the force/displacement transducer 12. The top view of the transducer of FIG. 4 will be the mirror image of the transducer shown in FIG. 3. Two pair of resistance strain gages are mounted to the beam 32 intermediate its ends, one pair of gages 35 and 36 on the outer side of the beam and another pair 37 and 38 (shown in dashed lines in the view of FIG. 4) mounted on the inner side of the beam, i.e., facing the patient's hand. The gages 35 and 36 measure tension at the outer side of the beam, while the gages 37 and 38 detect the compression on the inner side of the beam. The two tension and two compression gages are placed in opposite arms of a DC excited Wheatstone bridge such that a bending moment in the beam 32 produces a voltage signal at the output terminals of the bridge which is a substantially linear function of the force applied by adducting thumb. The four active strain gages provide four times the output signal of a single gage and thus provide a relatively high signal-to-noise ratio. Since all gages are on the same beam they are at the same temperature and compensation is not required. The bridge configuration of strain gages mounted on the beam also provides excellent linearity of signal response over a relatively wide range of applied forces. A schematic of the bridge circuit containing the strain gages 35, 36, 37 and 38 is shown in FIG. 5. A battery 40 provides a biasing voltage through a resistor 41 across the terminals of the bridge. The bridge circuit can be nulled by adjusting the potentiometer 42, controlled by the knob 20 on the face of the case 13, to provide a zeroing voltage through a resistor 43 to one of the output terminals of the bridge.

The output signal from the bridge on wires 44 and 45 is transmitted to the amplifier circuitry within the amplifier and low pass filter section labeled 29 in FIG. 5. The amplifier raises the output of the transducer to a level sufficient for analog to digital conversion. The signal on the wire 44 is passed to the positive input of a first operational amplifier 47, and the signal on the line 45 is passed to the positive input of a second operational amplifier 48. Capacitors 49 and 50 extend from the lines 44 and 45, respectively, to ground to filter out any radio frequency signals emitted by nearby electrosurgical units.

The outputs of the operational amplifiers 47 and 48 are fed back to the negative inputs of the respective amplifiers through resistors 51 and 52 of identical value, and an adjustable biasing resistor 53 is connected between these two, and controlled by the knob 21 on the face of the cabinet, to adjust the gain of the amplifier. The outputs of the amplifiers 47 and 48 are fed respectively through resistors 55 and 56 to the negative and positive inputs respectively of a third operational amplifier 57. A resistor 58 and a capacitor 59 are connected in parallel from the output to the negative input of the amplifier 57 to yield a low pass frequency characteristic preferably having an upper corner frequency of about 16 Hz. Small compensation capacitors 60, 61 and 63, each having a capacitance of about 1 nanofarad, are connected from the amplifiers 47, 48 and 57, respectively, to ground. A variable resistor 64 can be varied to allow adjustment of the common mode rejection ratio.

The output of the amplifier 57 is provided through a pair of resistors 66 and 67 to he positive input of another operational amplifier 69. Capacitors 70 and 71 and resistors 72 and 73 are connected to the amplifier to provide a second order Butterworth low pass filter with a preferred upper corner frequency of about 10 Hz.

The output from the amplifier 69 is provided on line 75 to an analog to digital converter 76 (e.g., National Semiconductor ADC. 0808). The converter 76 samples at a high enough rate to satisfy the Nyquist sampling criteria; for example, a sampling rate of 50 Hz. will provide satisfactory sampling since the output signal from the amplifier 69 will have any signals above 10 Hz. substanially attenuated. The converter 76 receives an input control signal from a microprocessor 78 on an input line 79, and delivers an 8 bit output on output lines 80. To start the conversion, the microprocessor 78 provides a pulse on the input line 79 and monitors the end of conversion output of the converter 76 provided on an output line 82. When this output goes low and subsequently returns high, the converted data is ready to be read by the microprocessor through the input port receiving the information on the lines 80.

The microprocessor 78 forms a portion of the controller 24 which controls the operation of the apparatus. A satisfactory controller can be formed using the Intel Corp. SDK-85 system design kit plus an additional 2,000 bytes of EPROM 84 for program storage. The SDK-85 kit includes an Intel 8085 microcomputer, Input/Output ports, 512 bytes of RAM, a hexadecimal keypad 17, programmable timers, a LED output display 18, and a 2,000 byte ROM 85 containing system monitor software. The programming of the microprocessor 78 sets the sampling rate of the converter 76 by controlling the internal timers.

The control signal output from the microprocessor 78 which initiates each stimulation pulse is passed through a pair of inverters 89 and 90 (e.g., 7404 inverters) and the control signals are then passed through a set of opto-isolators 91–95 (e.g., Monsanto 4N33 opto-isolators). The opto-isolators 91–95 serve to isolate the patient from electrical shock hazard by providing complete isolation of the line powered controller microcomputer system 24 from the nerve stimulator 26.

The stimulator shown within the dashed lines labeled 26 in FIG. 5 is adapted to generate a range of stimuli, including single twitch, train-of-four, and tetanic stimuli at 30, 100 and 200 Hz. Pulses are generated by a current differencing amplifier 100, configured as an oscillator, whose output is transmitted through an analog switch 101 which receives a gating signal on a line 102 from the microprocessor 78 through the opto-isolator 95. The output of the amplifier 100 will thus only be transmitted as long as the gate 101 is open, which, in turn, will depend on the type of stimulation being provided; for example, train-of-four stimuli requires a gate wide enough to pass four pulses at the preferred frequency of 2 Hz., whereas for a single twitch, the gate would be open only long enough for one pulse to pass. Tetanic stimulation is customarily applied for a period of five seconds. The frequency of pulses produced by the amplifier 100 is determined by the magnitude of the resistances in the feed back loops through diodes 104 and 105, in combination with the feed back capacitor 106 and resistor 107. The output of the amplifier 100 is also fed back through a resistor 108 in combination with another resistor 109 connected to the battery source. The output of the amplifier 100 is also fed back through one of the resistors 111-114 through four analog switches (CD4066) which are gated by one of the outputs of the opto-isolators 91–94, as determined by the particular control signal delivered from the microprocessor. The resistors 111 to 114 have various resistance values, thereby allowing the microprocessor to control the resistance in the feed back path about the amplifier 100 and the frequency at which pulses are produced by the amplifier.

The output of the analog gate 101 is passed through a resistor 117 to the high voltage pulse generation portion of the stimulator which includes transistors 118 and 119 and a 1 to 30 step-up transformer 120. The transistor 118 provides sufficient power to turn the power transistor 119 on and off, and a diode 121 is connected around the primary of the transformer 120 to protect the transistor 119 from damage due to ringing immediately after the transistor 119 has been turned off. For a 9-volt battery input, the step-up transformer provides pulses which are approximately 260 volts peak-to-peak. The output pulse waveform is biphasic, with the positive and negative portions of the pulse approximately of equal area so that substantially no net charge passes into the patient. It has been found that there is no difference in the response of the patient to biphasic or monophasic pulses which have similar magnitude and duration. The preferred width of the positive portion of the pulse is approximately 180 microseconds, which is within the 200 microsecond limit for accepted clinical practices. The current supplied at the output terminals 124, connected to the electrodes, is adjustably limited by a potentiometer 125.

Figure 6:
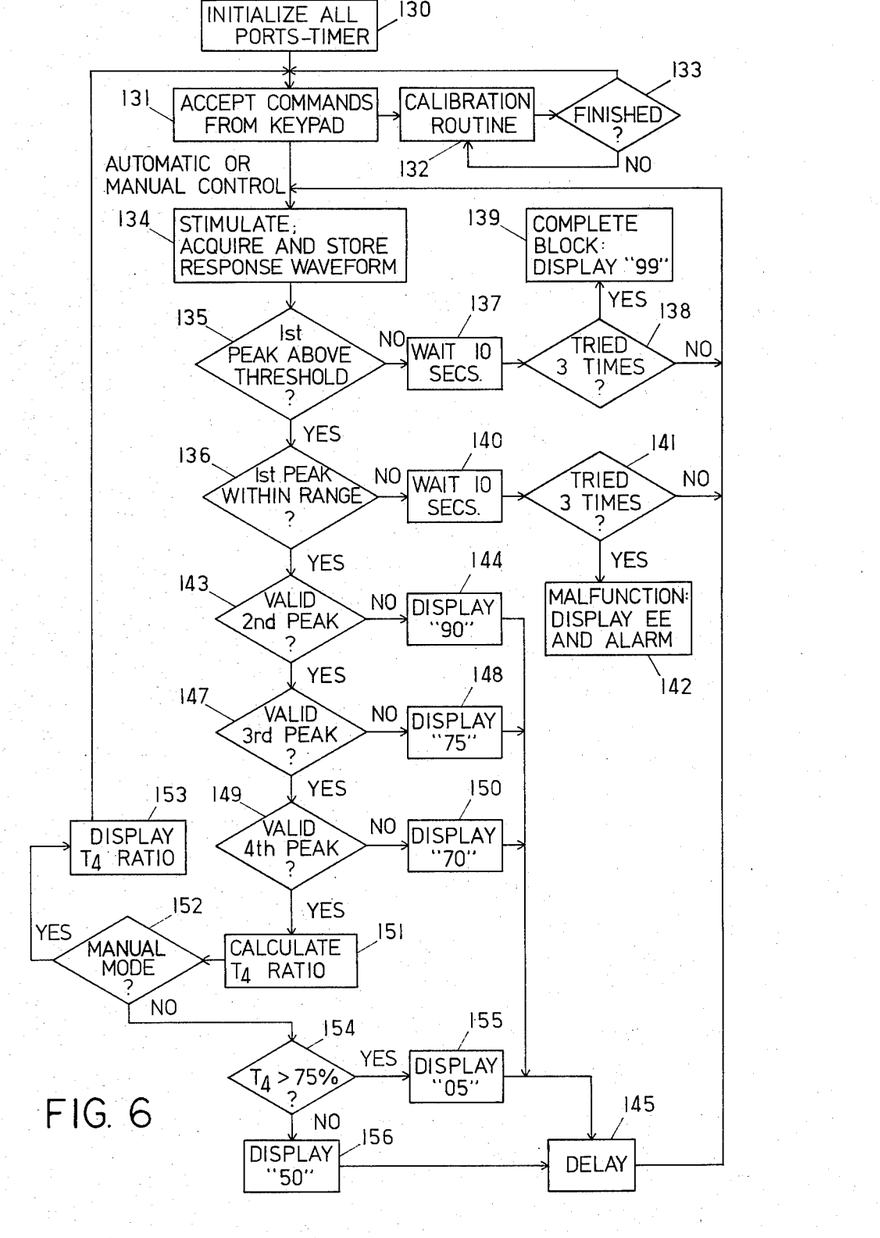
FIG. 6 is a flow chart illustrating the steps in the method of estimating the level of twitch response depression in a patient as implemented in the apparatus of the invention.

The sequence of steps by which the apparatus of the invention obtains an estimate of the degree of twitch height depression in a patient is shown in the flowchart of FIG. 6. The microprocessor 78 may be programmed to carry out the steps set forth in FIG. 6 automatically. The microcomputer 78 issues a control command signal that causes the nerve stimulator 26 to produce a train-of-four pulses at a frequency of 2 Hz. The responses by the patient are detected by the transducer 12 which provides an electrical response signal which will include a series of peaks corresponding in magnitude and duration to the motions of the patient's thumb. After passing through the amplifier and filter 29, the response signal is sampled and the magnitudes of the samples are converted to digital information which is supplied to the microcomputer within the controller 24. The responses are preferably stored in the computer system random access memory (RAM). The programming for the microprocessor performs calculations which determine the level of twitch height suppression based on the train-of-four response peaks and the ratio of the magnitude of the fourth pulse to the first pulse. This information is then displayed to the user on the display panel 18.

With reference to the flowchart in FIG. 6, the program must first initialize all ports as well as the programmable timer (block 130) that determines the analog to digital conversion sampling rate. The monitor then goes into a mode (block 131) in which it waits to accept commands from the user to be entered through the keyboard 17. As an example, in a train-of-four mode, the commands may be "C" for a calibration sequence, "4" for a manual train-of-four stimulation, and "A" for an automatic train-of-four mode.

For example, if the operator selects the calibration sequence, additional user commands may then be accepted. By pressing the "0" key the output of the force transducer system will be displayed in hexadecimal format. The operator can then null the output of the transducer to zero by turning the knob 20 on the front panel of the cabinet. By following this procedure, any preload that may be present on the transducer after it is affixed to the patient can be cancelled out. By pressing the "1" key, twitch stimuli at 2 Hz will be provided to the patient for ten seconds and the transducer output will be presented on the display. The operator may now scale the transducer output by adjusting the gain control knob 21 so that the stimulus response peaks are no greater than the 5 volt range of the analog to digital converter. After completing the calibration routine (block 132), if the operator decides that calibration is finished (133) he may press the "F" key which causes the control to again accept commands from the keypad. The operator may now choose between the manual or automatic mode. By pressing the "A" key, the automatic mode is selected which activates the nerve stimulator 26 to issue train-of-four stimuli. Sampling of the transducer signal at a sampling rate of 50 samples per second begins as soon as the stimulator turns on. The microcomputer within the controller 24 then stores preferably 150 data points (3 seconds of data) in RAM. These 150 data points will contain the train-of-four response (block 134).

The response is analyzed by first determining which of the four expected response peaks are present in response to the train-of-four stimuli. In the event that all four response peaks are present, the $T_4$ ratio—the ratio of the magnitude of the fourth peak to the first peak—is then calculated.

The first response peak is located using a search procedure to find the maximum magnitude over all of the 150 accumulated data points. When this peak is found, the amplitude and buffer location of the peak are stored. If the first peak is above a predetermined threshold level (block 135), the time at which the peak is found is then checked to see whether the peak has occurred within a proper period of time after stimulation (block 136) which generally should be within 500 milliseconds from the onset of stimulation. If both these conditions are found, the peak is a valid first peak in the train-of-four response. If the first peak is not above the threshold, the apparatus waits ten seconds (block 137) and then determines whether or not the stimulation routine has been tried three times (block 138); if so, the apparatus indicates to the operator that a complete neuromuscular block is present (block 139) by displaying a "99" on the display panel 18. If not, the stimulation, acquisition of data, and storage and analysis of the response waveform is repeated until the stimulation has been tried three times. If a peak is found, but the first peak is not within the proper time range, the apparatus waits 10 seconds (block 140) and then determines whether or not the stimulation has been tried three times (block 141) without finding a first peak within the required time range. If the stimulation has not been carried out three times, the stimulation, acquisition and storage of response data are repeated. If the stimulation has been tried for three times without finding a first peak within the required time range, the apparatus display indicates that a malfunction has occurred (block 142) by displaying an "EE" message on the display panel and sounding the alarm 22 to alert the operator that the apparatus is not obtaining valid information and cannot be relied on. For a 50 samples per second sampling rate by the analog to digital converter, the 500 millisecond period correponds to 25 samples. To be completely certain that a valid first peak is not missed, the time range within which the peak may be considered to be valid may be extended somewhat higher, for example up to the 45th sample. The threshold magnitude for the first peak is preferably set at 16% of the maximum value that a data point can have; this maximum value will correspond to the largest response peaks seen by the operator during the calibration routine. The 16% threshold level is chosen for convenience since background noise and unstimulated, random thumb movements will not exceed this threshold level. If a peak in the response signal exceeds the threshold, it is highly probable that the peak is due to a significant response by the patient and not to random movements or noise.

If a valid first peak is found, the apparatus stores the location and magnitude of this peak, calculates search parameters for a second peak and begins to search for the second peak. The second peak is accepted as valid if it exceeds a preset threshold magnitude (block 143). If no other peak is found which is above the threshold magnitude, there is no second peak and the apparatus displays a "90" on the display panel (block 144) which indicates that the patient is experiencing 90% of total twitch height suppression. The apparatus delays a preset period of time (block 145) before reinitiating the steps of stimulating the patient, and acquiring, storing and processing the response data.

If a valid second peak is found, the apparatus searches for a valid third peak (block 147) above a threshold magnitude, and if no valid third peak is found, "75" (block 148) is displayed on the display panel to indicate that 75% twitch height suppression is predicted. If a valid third peak is found the apparatus goes on to search for a valid fourth peak (block 149) above a threshold magnitude, and if no such peak is found, it displays "70" (block 150) on the display panel to indicate that 70% twitch height suppression is predicted. However, if all four peaks are present, the ratio of the fourth peak to the first peak (the $T_4$ ratio) is then calculated (block 151). If the apparatus is in the manual mode (block 152), the $T_4$ ratio is displayed on the display panel (block 153) and the apparatus resets to accept new commands from the keypad. However, if the apparatus is in the automatic mode, the apparatus automatically determines if the $T_4$ ratio exceeds 75% (block 154), and, if so, a "05" is displayed (block 155) on the display panel to indicate to the operator that less than 5% twitch height depression is predicted and the patient has recovered from the muscular relaxant. If the $T_4$ ratio is less than 75%, a "50" (block 156) is displayed on the display panel 18 to indicate to the operator that about a 50% twitch height depression is predicted. When the apparatus is in the automatic mode, after a determination is made that the $T_4$ ratio is greater or less than 75%, the apparatus delays for a preselected period of time, such as 5 to 10 minutes, and then automatically reapplies the stimuli to the patient to acquire new data.

The utilization of a microprocessor is desirable since it allows the system to be reprogrammed to operate in a different manner, for example, based on tetanic stimulation instead of train-of-four stimulation. Thus, the device can be utilized for clinical monitoring or muscle relaxant research. However, the operations carried out by the microprocessor can as well be performed utilizing hard wired components in a manner familiar to those skilled in the art.

It is apparent that the apparatus of the invention can similarly be utilized to deliver single twitch and tetanic stimulation to the patient as well as train-of-four. The output of the controller microprocessor 78 can be used to switch a chosen one of the resistors 111–114 into the feed back loop around amplifier 100 so as to change the period at which pulses are generated. The time period during which the gate 101 is opened can similarly be varied by the computer so that, for example, only a single pulse is passed—a single twitch stimulus—, or a rapid series of supramaximal pulses over a period of several seconds is passed—a tetanic stimulation.

If the baseline voltage from the transducer drifts, it can easily be compensated for by having the program within the microcomputor test the first few data points from the response waveform, which should be zero, to see if they are, in fact, zero. If not, a baseline shift has occurred, and the rest of the data can be shifted back into the correct position by substracting the average value of the first few data points from all of the response data. In addition, the microcomputer 78 in combination with a digital to analog converter (not shown) can inject a bucking voltage into the strain gage bridge while monitoring the transducer output so as to automatically null out any preload. The adjustment of the scale for the analog to digital converter 30 can also be accomplished automaticaly, in that the microcomputer 78 can control the gain of the amplifier by gating in different gain resistances with additional analog switches (not shown) in a manner similar to the analog switches 115 in combination with the resistances 111–114. By incorporation of such automatic adjustment of the system gain, the operator's task may be reduced to simply attaching the electrodes and the transducer to the patient and turning on the device.

It is understood that the invention is not confined to the particular construction and arrangement of parts herein illustrated and described, but embraces such modified forms thereof as come within the scope of the following claims.

We claim:

1. Apparatus for determining the level of neuromuscular blockage in a patient, comprising:
   (a) stimulator means responsive to a control signal for supplying an electrical pulse to electrodes attachable to a patient in response to the control signal received by the stimulator means;
   (b) force transducer means attachable to the thumb of a patient for measuring the adduction of the patient's thumb evoked in response to a stimulus applied by the electrodes, the force transducer means providing electrical output signals proportional to the magnitude of the thumb adduction;
   (c) controller means for comparing the output of a signal from the force transducer means with a threshold value, selected to be greater than background noise and unstimulated, random thumb movements, to determine if a significant response is present and for providing a magnitude output signal indicative of whether the magnitude of the signal from the force transducer means is less than or greater than the selected threshold value, the controller means also providing a control signal to the stimulator means to initiate stimulation of the patient; and
   (d) display means receiving the magnitude output signal from the controller means for providing a visual display to the operator in response to the magnitude output signal to indicate to the operator whether the magnitude of the transducer means output signal is less than or greater than the selected threshold value.

2. The apparatus of claim 1 further including:
   (1) filter means for filtering the output signal from the force transducer means to substantially attenuate frequencies in such signal above approximately 10 Hz; and
   (2) analog-to-digital converter means for sampling the signal passed through the filter means and for providing a digitized output signal indicative of the magnitude of the signal passed through the filter means at the sample times;
   the controller means receiving the output signal of the analog-to-digital converter means and comparing this digitized signal with a selected digitized threshold value to determine if a significant response is present and providing a digitized magnitude output signal to the display means which is indicative of whether the magnitude of the signal from the converter means is less than or greater than the selected threshold value, and wherein the display means is responsive to the digitized magnitude output signal received from the controller means.

3. The apparatus of claim 2 wherein the controller means provides the digitized magnitude output signal to the display means only if the digitized signal received by the controller means from the converter means is provided at a point in time which is less than a selected period of time after the control signal is provided to the stimulator means to initiate stimulation.

4. The apparatus of claim 1 wherein the stimulator means is responsive to the control signal for supplying 4 biphasic control pulses in regular secession over a period of approximately 2 seconds; and wherein the controller means further determines whether there is a first response peak in the signal received from the force transducer means which is above a selected threshold value corresponding to a significant response and, if not, provides a magnitude output signal to the display means to cause the display means to indicate that 99% twitch height depression is predicted; and if the first response peak is above the threshold value, the controller means determines if there is a second response peak above a selected threshold value corresponding to a significant response and, if not, provides a magnitude output signal to the display means to cause the display means to indicate that 90% twitch height depression is predicted; and if the second peak is above the selected threshold value, the controller means determines if there is a third response peak above a selected threshold value corresponding to a significant response, and, if not, provides a magnitude output signal to the display means to cause the display means to indicate that 75% twitch height depression is predicted; and if the third peak is above the selected threshold value, the controller means determines if there is a fourth response peak above a selected threshold value corresponding to a significant response, and, if not, provides a magnitude output signal to the display means to cause the display means to indicate that 70% twitch height depression is predicted; and, if the fourth peak is above the selected threshold value, the controller means calculates the ratio of the magnitude of the fourth response peak to the first response peak, and if this ratio is above 75%, it provides a magnitude output signal to the display means to cause the display means to indicate that not more than 5% twitch height depression is predicted; whereas, if the ratio of the fourth peak to the first peak is less than 75%, the controller means provides a magnitude output signal to the display means to cause the display means to indicate to the operator that at least 50% twitch height depression is predicted.

5. The apparatus of claim 2 or 3 wherein the controller means includes a microprocessor receiving the output of the analog to digital converter means, and including internal timer means for controlling the times at which control signal pulses are provided to the stimulator means and for timing the period between the control signal pulses supplied to the stimulator means and the response peaks measured by the force transducer means and converted to digitized form by the analog to digital converter means.

6. The apparatus of claim 1 wherein the stimulator means includes electrical circuit means for generating a series of biphasic pulses in response to control signals provided from the controller means, and a battery which supplies the power required to deliver the stimulation pulses to the electrodes attachable to the patient, and further including opto-isolators connected to supply the control signals from the controller means to the stimulator means so as to completely isolate the stimulator means from any stray voltages associated with the controller means.

7. The apparatus of claim 1 wherein the force transducer means includes a circuit having resistances which change in response to the force supplied by the thumb of the patient and wherein voltage across the resistances within the force transducer means is provided by a battery at low voltage so that the force transducer means is isolated from line power to minimize the potential of shocks to the patient.

8. The apparatus of claim 7 wherein the transducer means includes four variable resistances connected together in a Wheatstone bridge configuration and supplied with bias current from a battery across two terminals of the bridge, with the output of the bridge being taken across the other terminals of the bridge and being proportional to the force applied by the patient's thumb in response to the stimulus applied to the patient.

9. The apparatus of claim 1 wherein the force transducer means includes:
(1) a resiliently bendable beam having two flat sides and sized to extend from the wrist to the end of the thumb of the patient;
(2) a wrist collar mounted to one end of the bendable beam and adapted to be releasably secured to the wrist of the patient;
(3) a thumb collar mounted to the other end of the bendable beam and adapted to releasably secure to the thumb of the patient;
(4) two pair of electrical resistance strain gages mounted on opposite sides of the beam intermediate its ends such that the pairs are substantially coincident with one another.

10. The apparatus of claim 9 wherein the transducer means further includes circuit means for connecting the strain gages in a bridge circuit with the gages in each pair in opposite arms of the bridge; and a battery connected to apply a biasing voltage across two terminals of the bridge formed by the strain gages with the output across the other terminals of the bridge being proportional to the bending of the beam in response to force applied by the thumb of the patient.

11. The apparatus of claim 1 wherein the controller means controls the stimulator means to provide a train of electrical pulses to the electrodes attachable to a patient and sequentially compares the response to each pulse in the train to a selected threshold value and provides a magnitude output signal indicative of whether the magnitude of the signal from the force transducer means in response to each pulse in the train is less than or greater than the selected threshold value.

12. A device for monitoring the response of a patient to stimulation of the ulnar nerve, comprising:
(a) a resiliently bendable beam having two flat sides and sized to extend from the wrist to the end of the thumb of the patient;
(b) a wrist collar mounted to one end of the bendable beam and adapted to be releasably secured to the wrist of the patient;
(c) a thumb collar mounted to the other end of the bendable beam and adapted to be releasably secured to the thumb of the patient;
(d) two pair of electrical resistance strain gages mounted on opposite sides of the beam intermediate its ends such that the pairs are substantially coincident with one another, one pair of gages mounted on the outer side of the beam measuring the tension as the beam bends and the other pair of gages on the inner side of the beam measuring compression as the beam bends;
(e) circuit means for connecting the two pair of strain gages in a bridge circuit with the gages in each pair being in opposite arms of the bridge; and
(f) a battery connected to apply a biasing voltage across two terminals of the bridge formed by the strain gages with the output across the other terminals of the bridge being substantially proportional to the bending of the beam in response to force applied by the thumb of the patient.

13. A method for determining the degree of neuromuscular block in a patient, comprising the steps of:
(a) providing a train of four electrical stimulus pulses to the ulnar nerve of a patient over approximately a two second period of time;
(b) measuring the magnitude of the thumb adduction responses of the patient to the stimulus pulses and providing an electrical signal proportional thereto;
(c) comparing a first peak of magnitude of thumb adduction response signal with a preselected threshold value corresponding to a significant response, and, if the peak is below the preselected threshold value, displaying indicia to an operator to indicate that substantially complete twitch height depression is estimated;

(d) if the first response magnitude peak is above the preselected threshold value, then comparing a second response magnitude peak with a preselected value corresponding to a significant response and, if the peak is below the preselected threshold value, displaying indicia to an operator indicating that 90% twitch height depression is estimated;

(e) if the second response magnitude peak is above the preselected threshold value, then comparing a third response magnitude peak to another preselected threshold value corresponding to a significant response and, if the peak is below the preselected threshold value, displaying indicia to an operator indicating that 75% twitch height depression is estimated;

(f) if the third response magnitude peak is above the preselected threshold value, then comparing a fourth response magnitude peak to another preselected threshold value corresponding to a significant response and, if the fourth response magnitude peak is below the preselected threshold value, displaying indicia to an operator indicating that 70% twitch height depression is estimated;

(g) if the fourth response magnitude peak is above the preselected threshold value, then calculating the numerical ratio of the magnitude of the fourth response magnitude peak to the magnitude of the first response magnitude peak; and (h) comparing the ratio of the fourth to first response magnitude peaks to 0.75, and displaying indicia to an operator indicating that at least 50% twitch height depression is estimated if the ratio of the fourth to first peaks is below 0.75 and displaying indicia to an operator indicating that not more than 5% twitch height depression is estimated if the ratio of the fourth to first peaks is above 0.75.

14. The method of claim 13 including, after the step of determining that the first peak in the response magnitude is above the preselected threshold value, the step of determining whether the first response magnitude peak occurs within a preselected range of time after the application of the first stimulus pulse to the patient, and, if not, providing an output display to the operator indicating that a malfunction has occurred.

* * * * *